US008664618B2

(12) United States Patent
Yao

(10) Patent No.: US 8,664,618 B2
(45) Date of Patent: Mar. 4, 2014

(54) SPHERICAL ROTATIONAL RADIATION THERAPY APPARATUS

(75) Inventor: Jonathan Yao, San Jose, CA (US)

(73) Assignee: LinaTech LLC, Sunnyvale, CA (US)

( * ) Notice: Subject to any disclaimer, the term of this patent is extended or adjusted under 35 U.S.C. 154(b) by 177 days.

(21) Appl. No.: 13/470,504

(22) Filed: May 14, 2012

(65) Prior Publication Data

US 2013/0256551 A1    Oct. 3, 2013

Related U.S. Application Data

(60) Provisional application No. 61/618,717, filed on Mar. 31, 2012.

(51) Int. Cl.
 *G01T 1/00* (2006.01)
(52) U.S. Cl.
 USPC ............................................ 250/393; 378/65
(58) Field of Classification Search
 USPC .................. 250/393; 378/4, 15, 196, 197, 65
 See application file for complete search history.

(56) References Cited

U.S. PATENT DOCUMENTS

| | | | | |
|---|---|---|---|---|
| 5,982,844 A * | 11/1999 | Tybinkowski et al. | ............ | 378/4 |
| 6,188,743 B1 * | 2/2001 | Tybinkowski et al. | ............ | 378/4 |
| 6,337,894 B1 * | 1/2002 | Tybinkowski et al. | ............ | 378/4 |
| 6,580,777 B1 * | 6/2003 | Ueki et al. | ...................... | 378/17 |
| 6,969,194 B1 * | 11/2005 | Nafstadius | .................... | 378/197 |
| 7,983,380 B2 * | 7/2011 | Guertin et al. | ..................... | 378/4 |
| 2006/0285647 A1 * | 12/2006 | Yunker | ......................... | 378/197 |
| 2009/0003522 A1 * | 1/2009 | Chien et al. | ..................... | 378/65 |
| 2009/0034887 A1 * | 2/2009 | Fujikawa et al. | .............. | 384/99 |
| 2009/0074150 A1 * | 3/2009 | Jaffray et al. | ................. | 378/197 |
| 2010/0195792 A1 * | 8/2010 | Kunz et al. | ..................... | 378/65 |
| 2012/0305793 A1 * | 12/2012 | Schiefer | ........................ | 250/394 |

* cited by examiner

*Primary Examiner* — David Porta
*Assistant Examiner* — Taeho Jo
(74) *Attorney, Agent, or Firm* — Chein-Hwa Tsao; C H Emily LLC

(57) ABSTRACT

A spherical rotational radiation therapy apparatus (SRRTA) with single spherical rotation center (SRC) is proposed. Referencing a combined X-Y-Z Cartesian and (r-α-β-γ) polar coordinates. The SRRTA includes a multi-axial gantry with rotatable proximal face around gantry bore; the proximal gantry face has at least one rotatable, along α-coordinate, pair of therapeutic level radiation-generating accelerator and image detector defining a therapeutic level radiation axis between the two; at least two arc-shaped sub-rails on the proximal gantry face; at least two rotationally slidable, against the arc-shaped sub-rails thus along α-coordinate, pairs of imaging level radiation-generating accelerators and image detectors defining an imaging level radiation axis between the two; the therapeutic level radiation axes and all imaging level radiation axes are configured to intersect at a single SRC along the longitudinal bore axis; an X-axis gantry pivoting driving mechanism is provided for driving the distal end of the multi-axial gantry.

7 Claims, 5 Drawing Sheets

SPHERICAL ROTATIONAL RADIATION THERAPY APPARATUS

CROSS REFERENCE TO RELATED APPLICATIONS

This application is based upon and claims the priority of a previously filed provisional patent application entitled "A Sphere Rotational Radiation Therapy Apparatus" by Jonathan Yao with application No. 61/618,717, filing date Mar. 31, 2012 whose content is herein incorporated by reference for all purposes.

FIELD OF INVENTION

This invention relates generally to the field of medical apparatus. More specifically, the present invention is directed to a multi-rotational axis positioning radiation therapy apparatus for performing image guided radiation therapy (IGRT) in conjunction with an electronic radiation therapy controller.

BACKGROUND TECHNOLOGY

While conducting radiation therapy of a patient tumor (target zone, or target organ) accurate location of the tumor is necessary. For location in a 3-dimensional space, a physician or radiologist at first scans and acquires, in a Computed Tomography (CT) room, a CT image data set of the patient then reconstructs, via a geometric computational algorithm, a corresponding 3-dimensional graphic image of the patient. The patient tumor can now be located by its 3-dimensional coordinates. Next, the physician or radiologist moves the patient into an accelerator room and recovers the tumor location by positioning an isocenter of the accelerator so that it accurately coincides with the 3-dimensional coordinates of the patient tumor. Finally, the radiation therapy commences. At present, the accelerator of radiation therapy equipment can only rotate around a horizontal axis generally parallel to the patient body (the Z-axis). In addition, radiation beams emanated from the accelerator are also constrained to a plane perpendicular to the Z-axis lacking the freedom of choosing their radiation incident angle. Consequently, such constraints of the present-day radiation therapy equipment impose substantial functional limitations to the diagnosis and directional radiation treatment of diseases.

Targeting the above-described constraints, a corresponding set of solutions have been proposed. The solutions include hanging the accelerator upon a sliding track that is parallel to the Z-axis for a reciprocating sliding movement along the Z-axis plus a pendulum-like movement of the accelerator head in a YZ-plane (Y-axis being vertical) whereby realizing a radiation with 3-dimensional multi-incident angle. However, firstly the heavy weight of the accelerator causes the accelerator-hanging mechanism and its associated driving mechanism to become highly complex with high production cost. Secondly, the pendulum-like movement of the accelerator head can cause instability of the radiation beams. Thirdly, the tight coupling between the accelerator and its driving mechanism can cause interference to the whole treatment system further increasing production difficulty and cost. Fourthly, it is noted that the treatment system has an integral digital image detection planar board that functions to detect radiation from the accelerator and to render its radiation image. Thus, the pendulum-like movement of the accelerator head would cause a loss of real-time functional synchrony between the accelerator and the digital image detection planar board, affecting the ability of the treatment system to perform treatment with real-time diagnosis and compensation.

To solve the above described problems, the present invention proposes a 4-dimensional (three-dimensional space+time) positioning radiation therapy apparatus that, through tracking in a 4-dimensional space, allows the administered radiation dosage to vary dynamically according to the space-time trajectory of the target organ to realize accurate treatment with simple, easy to manufacture structure while simultaneously shortening treatment time and saving cost.

SUMMARY OF THE INVENTION

A gantry based radiation therapy mechanism with a single spherical rotation center-rooted spherical rotational radiation therapy apparatus (SRRTA) is proposed. The gantry has a hollow cylindrical gantry bore. expressing the SRRTA in a combined X-Y-Z Cartesian coordinates and an accompanying polar coordinates (r-$\alpha$-$\beta$-$\gamma$) is adopted as a three-dimensional reference frame where the Z-axis is parallel to a longitudinal axis of the hollow cylindrical gantry bore and pointing from the proximal end of the gantry toward its distal end, the Y-axis is pointing vertically upwards and the X-axis is pointing horizontally and parallel to a proximal end face of the gantry and wherein $\alpha$ is an angular coordinate in the X-Y plane, $\beta$ is an angular coordinate in the Y-Z plane and $\gamma$ is an angular coordinate in the Z-X plane. The SRRTA includes:

a) A multi-axial gantry of a substantially cylindrical shape with an annular X-Y cross section and a hollow cylindrical bore with a longitudinal bore axis. The proximal face of the multi-axial gantry is made rotatable around the longitudinal bore axis thus along $\alpha$-coordinate.

b) The proximal face of the multi-axial gantry has:

b1) One or more rotatable annularly opposing pairs of therapeutic level radiation-generating accelerator and its corresponding therapeutic level radiation-image detector. The rotation is around the longitudinal bore axis thus along $\alpha$-coordinate. Thus, each pair defines a therapeutic level radiation-imaging pair and a rotatable therapeutic level radiation axis between the two.

b2) At least two annularly opposing arc-shaped sub-rails mounted on the proximal gantry face and centered around the longitudinal bore axis.

b3) At least two rotationally slidable annularly opposing pairs of imaging level radiation-generating accelerators and their corresponding imaging level radiation-image detectors. The rotational sliding movement is against the arc-shaped sub-rails thus along $\alpha$-coordinate. Thus, each pair defines an imaging level radiation-imaging pair and a rotatable imaging level radiation axis between the two.

c) The Z-coordinates of all the therapeutic level radiation-imaging pairs and all the imaging level radiation-imaging pairs are selected such that all the therapeutic level radiation axes and all the imaging level radiation axes intersect at a single spherical rotation center (SRC) located at a predetermined point along the longitudinal bore axis.

Upon placement of a patient with his target organ coinciding with the SRC and upon interfacing the SRRTA with an external electronic radiation therapy controller (ERTC), the SRRTA functions to perform 4-dimensional image guided radiation therapy (IGRT) with:

(A) A global $\alpha$-radiation angle adjustment mode where the $\alpha$-coordinates of all therapeutic level radiation axes and all imaging level radiation axes are dynamically changed in unison through rotation of the proximal gantry face; and/or (B) An individualized α-imaging angle adjustment mode where the α-coordinate of each individual imaging level radiation axis is dynamically changed, through the rotation of its corresponding imaging level radiation-imaging pair against the arc-shaped sub-rails, independent of other imaging level radiation axes and all the therapeutic level radiation axes.

As a more detailed embodiment, the SRRTA further includes an X-axis gantry pivoting base support mechanism coupled to and supporting the multi-axial gantry and an X-axis gantry pivoting driving mechanism coupled to and driving the distal end of the multi-axial gantry. The multi-axial gantry has a proximal sub-gantry (PSG) and a distal sub-gantry (DSG) with:

The PSG rotatably, around the longitudinal bore axis, supported by the DSG through a bearing interface between the PSG and the DSG.

The DSG pivotably, around a DSG-rotational axis parallel to the X-axis thus along the β-coordinate, supported by the X-axis gantry pivoting base support mechanism. Additionally, the DSG is driven through the β-coordinate by the X-axis gantry pivoting driving mechanism.

As a result, the SRRTA additionally functions to perform IGRT with:

(C) A global β-radiation angle adjustment mode where the β-coordinates of all therapeutic level radiation axes and all imaging level radiation axes are dynamically changed in unison through rotation around the DSG-rotational axis.

As a more detailed embodiment to insure structural rigidity of the multi-axial gantry and locational accuracy of the SRC, the X-axis gantry pivoting base support mechanism is configured to have at least two base support mechanisms each having a pivot-bearing engaging the DSG and a support strut supporting the pivot-bearing.

To further strengthen structural rigidity of the multi-axial gantry and increase locational accuracy of the SRC, the X-axis gantry pivoting base support mechanism further includes a bottom base for affixing the support struts upon it.

In a more specific embodiment, the proximal gantry face is configured to have one annularly opposing pair of therapeutic level radiation-generating accelerator and its corresponding therapeutic level radiation-image detector.

In a more specific embodiment, the proximal gantry face is configured to have two annularly opposing arc-shaped sub-rails.

In yet another more specific embodiment, each arc-shaped sub-rail is configured to subtend an α-range from about 20 degrees to about 150 degrees.

BRIEF DESCRIPTION OF THE DRAWINGS

To describe numerous embodiments of the present invention, reference is made to the accompanying drawings. However, these drawings are not to be considered limitations in the scope of the invention, but are merely illustrative.

DETAILED DESCRIPTION OF SPECIFIC EMBODIMENTS

Figure 1:
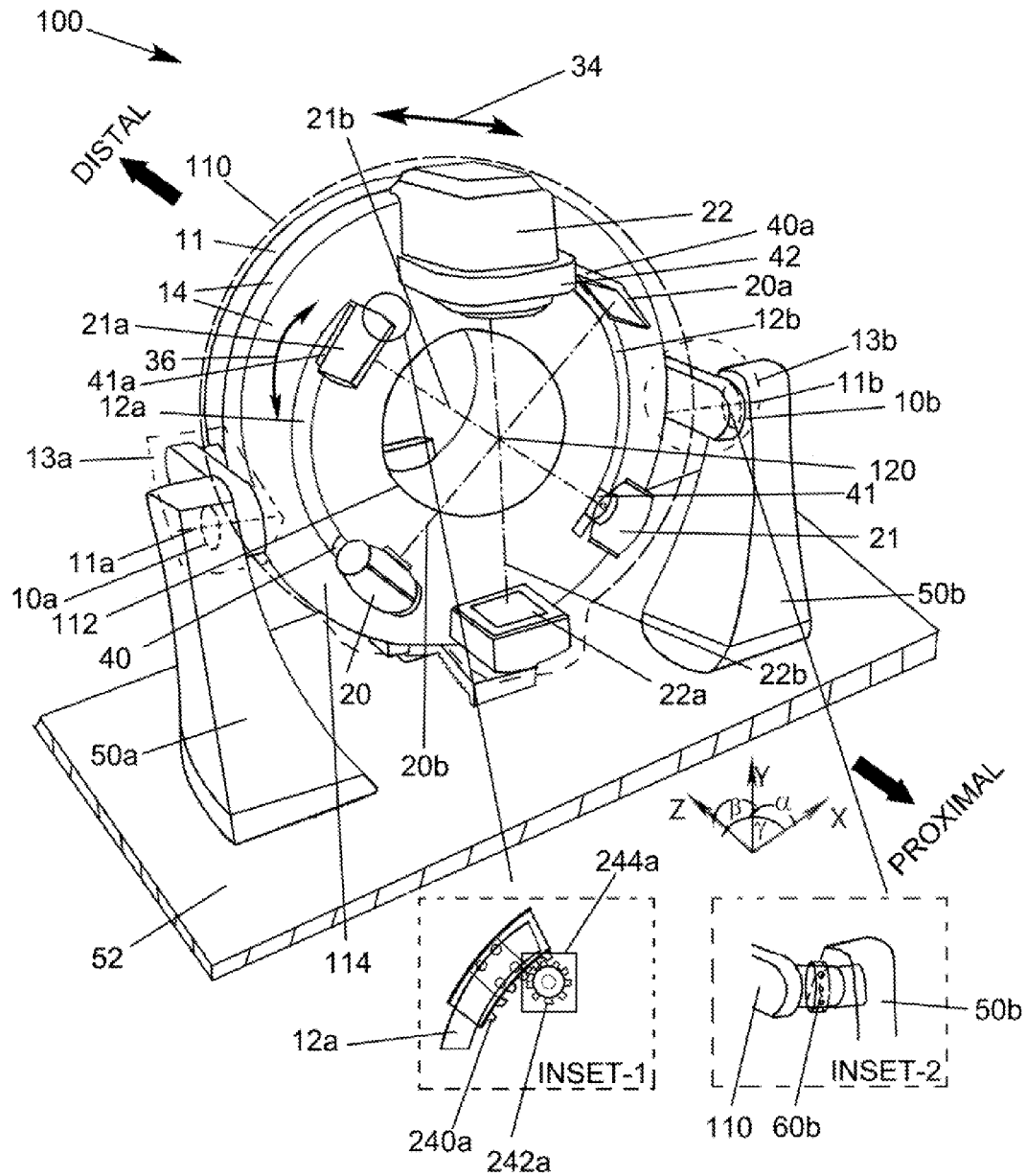
FIG. 1 illustrates a front perspective view of an embodiment of the present invention spherical rotational radiation therapy apparatus (SRRTA)

The following specific embodiments, in combination with the accompanying drawings, serve to further explain the present invention in details. FIG. 1 illustrates a front perspective view of an embodiment of the present invention spherical rotational radiation therapy apparatus (SRRTA) 100. To those skilled in the art, the SRRTA 100 is a gantry based radiation therapy apparatus with a multi-axial gantry 110 of a substantially cylindrical shape with an annular X-Y cross section. The multi-axial gantry 110 has a hollow cylindrical bore 112. The hollow cylindrical bore 112 has a longitudinal bore axis 112a (see FIG. 2). Notice that the multi-axial gantry 110 includes a proximal sub-gantry (PSG) 14 and a distal sub-gantry (DSG) 11 with the PSG 14 rotatably, around the longitudinal bore axis 112a, supported by the DSG 11 through a bearing interface between them. This arrangement thus supports a Z-rotation 36 of the PSG 14. As directional references, the proximal end and distal end of the multi-axial gantry 110 are also indicated with their corresponding arrows. For convenience of description, the SRRTA 100 is expressed in a combined X-Y-Z Cartesian coordinates and an accompanying polar coordinates (r-α-β-γ) where the Z-axis is parallel to a longitudinal axis of the hollow cylindrical bore 112 and pointing from the proximal end of the multi-axial gantry 110 toward its distal end, the Y-axis is pointing vertically upwards and the X-axis is pointing horizontally and parallel to a proximal gantry face 114 of the multi-axial gantry 110 and wherein α is an angular coordinate in the X-Y plane, β is an angular coordinate in the Y-Z plane and γ is an angular coordinate in the Z-X plane.

As illustrated in FIG. 1, the SRRTA 100 includes a therapeutic level radiation-generating accelerator 22 for generating and directing a radiation of therapeutic wavelength and power level along a rotatable therapeutic level radiation axis 22b. An example of the therapeutic level radiation-generating accelerator 22 can be a Mega-Volt level accelerator. The SRRTA 100 also includes the following:

(a) A therapeutic level accelerator support frame 42 supporting the therapeutic level radiation-generating accelerator 22. Although not visible here, a multi-leaf radiation collimator is deployed below the therapeutic level accelerator support frame 42 for constraining and defining a cross sectional area and shape for radiation passage. In an embodiment the multi-leaf radiation collimator has a plurality of electrically individually activatable leaves. In another embodiment, although not visible here either, at least one camera head can be deployed upon the multi-leaf radiation collimator.

(b) The proximal gantry face 114 has:

(b1) An annularly opposing pair of therapeutic level radiation-generating accelerator 22 and its corresponding therapeutic level radiation-image detector 22a. This pair (22, 22a) is configured to be rotatable, around the longitudinal bore axis 112a thus along α-coordinate. Thus, this pair defines a therapeutic level radiation-imaging pair and the rotatable therapeutic level radiation axis 22b between the two. For those skilled in the art, the therapeutic level radiation-image detector 22a can be made of a Mega-Volt (MV) radiation level digital image detection planar board and its structure can be of a fixed type, a foldable type or a protrusion-retraction type. Additional therapeutic level radiation-imaging pairs can be added upon the proximal gantry face 114 if so desired.

(b2) At least two annularly opposing arc-shaped sub-rails 12a, 12b are mounted on the proximal gantry face 114 and centered around the longitudinal bore axis 112a.

(b3) At least two annularly opposing pairs of imaging level radiation-generating accelerators (20, 21) and their corresponding imaging level radiation-image detectors (20a, 21a). The imaging level radiation-generating accelerators (20, 21) are respectively coupled to the arc-shaped sub-rail 12a with an imaging level accelerator support frame 40 and the arc-shaped sub-rail 12b with an imaging level accelerator support frame 41. The imaging level radiation-image detectors (20a, 21a) are respectively coupled to the arc-shaped sub-rail 12b with an imaging level detector support frame 40a and the arc-shaped sub-rail 12a with an imaging level detector support frame 41a. Each one of the two pairs is configured to be rotationally slidable against the arc-shaped sub-rails 12a, 12b thus along α-coordinate. Structurally, the arc-shaped sub-rails (12a, 12b) can be made of a guide rail or a sliding groove. In one embodiment, each arc-shaped sub-rail (12a or 12b) subtends an α-range from about 20 degrees to about 150 degrees. Thus, the pair (20, 20a) defines an imaging level radiation-imaging pair and a rotatable imaging level radiation axis 20b between the two. Likewise, the pair (21, 21a) defines another imaging level radiation-imaging pair and a rotatable imaging level radiation axis 21b between the two. To those skilled in the art, an example of the rotational mechanism is illustrated in INSET-1 where the arc-shaped sub-rail 12a has a mounted sub-rail gear track 240a. Correspondingly, the imaging level radiation-image detector 21a has a mounted gear motor 244a with a drive gear 242a that is coupled to the sub-rail gear track 240a. The rotation of the gear motor 244a then causes a sliding movement of the imaging level radiation-image detector 21a against the arc-shaped sub-rail 12a. An example of the imaging level radiation-generating accelerators (20, 21) can be a Kilo-Volt level accelerator. An example of the imaging level radiation-image detectors (20a, 21a) can be a digital image detection planar board for detecting Kilo-Volt level radiation and rendering of its radiation image.

(c) The Z-coordinates of the therapeutic level radiation-imaging pair (22, 22a) and all the imaging level radiation-imaging pairs [(20, 20a) and (21, 21a)] are selected such that, as illustrated in FIG. 1 and later in FIG. 2, the therapeutic level radiation axis 22b and all the imaging level radiation axes (20b, 21b) intersect at a single spherical rotation center (SRC) 120 located at a predetermined point along the longitudinal bore axis 112a.

(d) X-axis gantry pivoting base support mechanisms 13a, 13b and an X-axis gantry pivoting driving mechanism driving the accelerator support frame 42, hence the therapeutic level radiation-generating accelerator 22, into a rotational movement around the X-axis, as signified by a double-headed arrow of X-rotation 34. Some examples of the X-axis gantry pivoting driving mechanism will be presently illustrated. The two base support mechanisms 13a, 13b are provided to insure structural rigidity of the multi-axial gantry 110. The base support mechanism 13a has a pivot-bearing 10a (centered around a DSG-rotational axis 11a) engaging the DSG 11 and a support strut 50a supporting the pivot-bearing 10a. Similarly, the base support mechanism 13b has a pivot-bearing 10b (centered around a DSG-rotational axis 11b) engaging the DSG 11 and a support strut 50b supporting the pivot-bearing 10b. To those skilled in the art, a more detailed example of the base support mechanism 13b is illustrated in INSET-2 where the base support mechanism 13b has a bearing element 60b rotatably coupling the multi-axial gantry 110 to the support strut 50b. If necessary, more base support mechanisms can be added to further strengthen the structural rigidity of the multi-axial gantry 110.

(e) A bottom base 52 upon which the support struts 50a 50b are affixed to.

Figure 2:
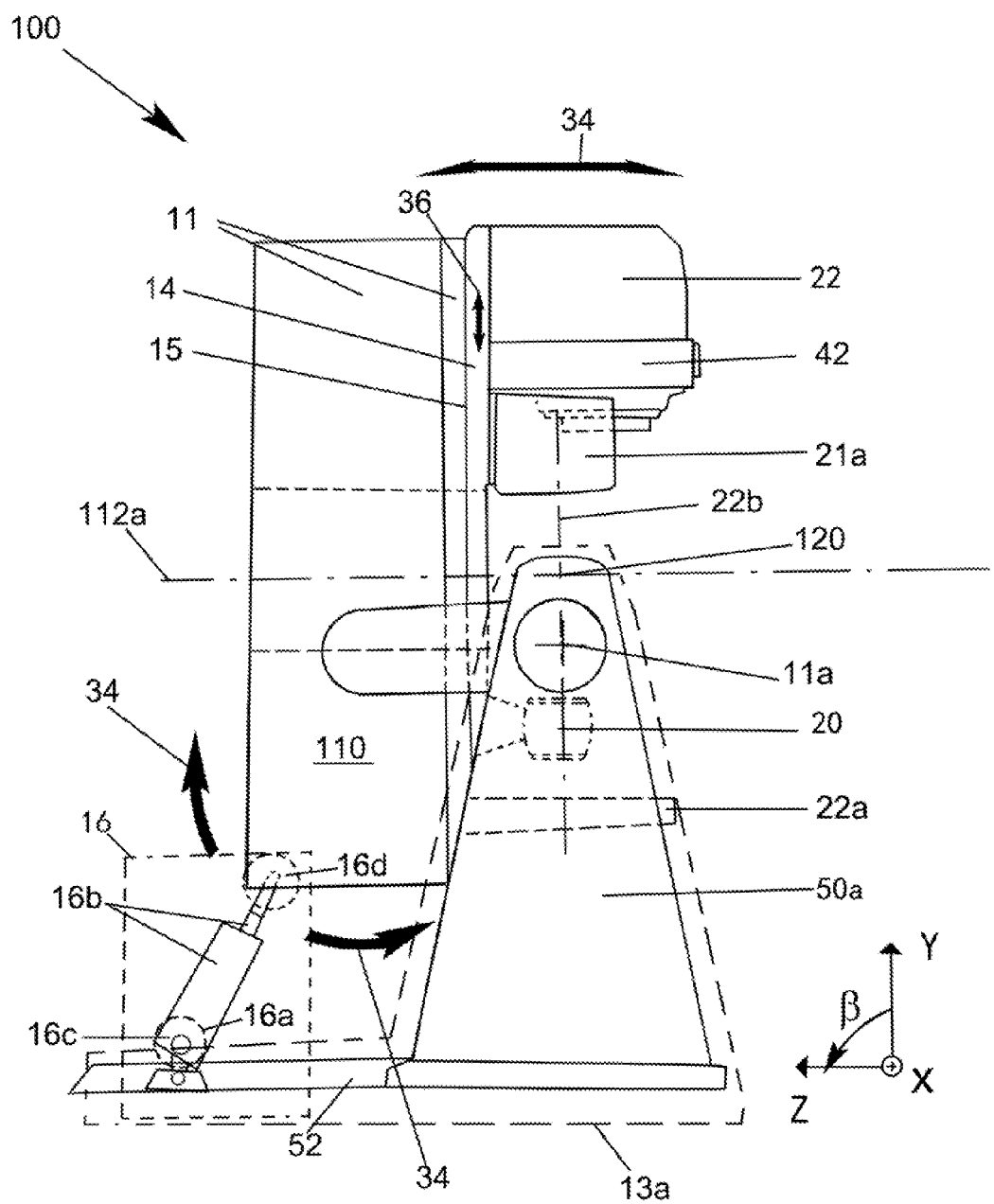
FIG. 2 illustrates a side view of another embodiment of the present invention SRRTA.

FIG. 2 illustrates a side view of another embodiment of the present invention SRRTA 100. An example of the previously described the X-axis gantry pivoting driving mechanism is an X-axis gantry pivoting hydraulic driving mechanism 16 coupled to and driving the distal end of the multi-axial gantry 110. The X-axis gantry pivoting hydraulic driving mechanism 16 has a hydraulic piston 16b, a hydraulic drive linkage 16d and a hydraulic drive linkage 16c coupling the multi-axial gantry 110 to the bottom base 52. The X-axis gantry pivoting hydraulic driving mechanism 16 also has a hydraulic compressor 16a driving the hydraulic piston 16b thus effecting the X-rotation 34 of the multi-axial gantry 110. As a side remark, a bearing interface 15 can be seen here between the PSG 14 and the DSG 11. As another side remark, the DSG 11 can be seen to be pivotably, around the DSG-rotational axis 11a, driven through β-coordinate by the X-axis gantry pivoting hydraulic driving mechanism 16.

Figure 3:
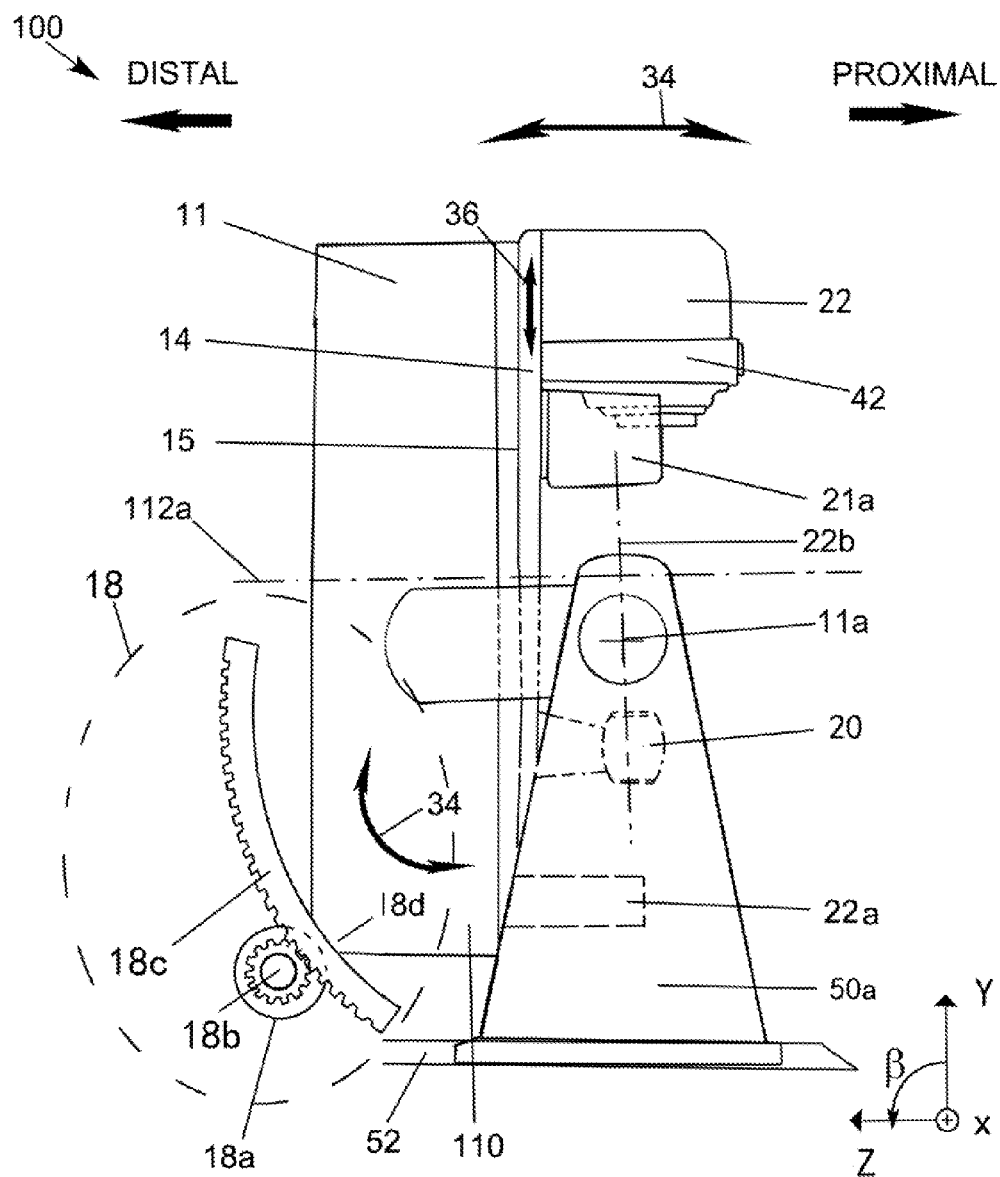
FIG. 3 illustrates a side view of another embodiment of the present invention SRRTA.

FIG. 3 illustrates a side view of another embodiment of the present invention SRRTA 100. Another example of the previously described the X-axis gantry pivoting driving mechanism is an X-axis gantry pivoting gear driving mechanism 18 coupled to and driving the distal end of the multi-axial gantry 110. The X-axis gantry pivoting gear driving mechanism 18 has a gear drive linkage 18d, an arc-shaped gear track 18c and a drive gear 18b coupling the multi-axial gantry 110 to the bottom base 52. The X-axis gantry pivoting gear driving mechanism 18 also has a drive motor 18a driving the drive gear 18b thus effecting the X-rotation 34 of the multi-axial gantry 110. Hence, the DSG 11 can be seen to be pivotably, around the DSG-rotational axis 11a, driven through β-coordinate by the X-axis gantry pivoting gear driving mechanism 18.

Figure 3A:
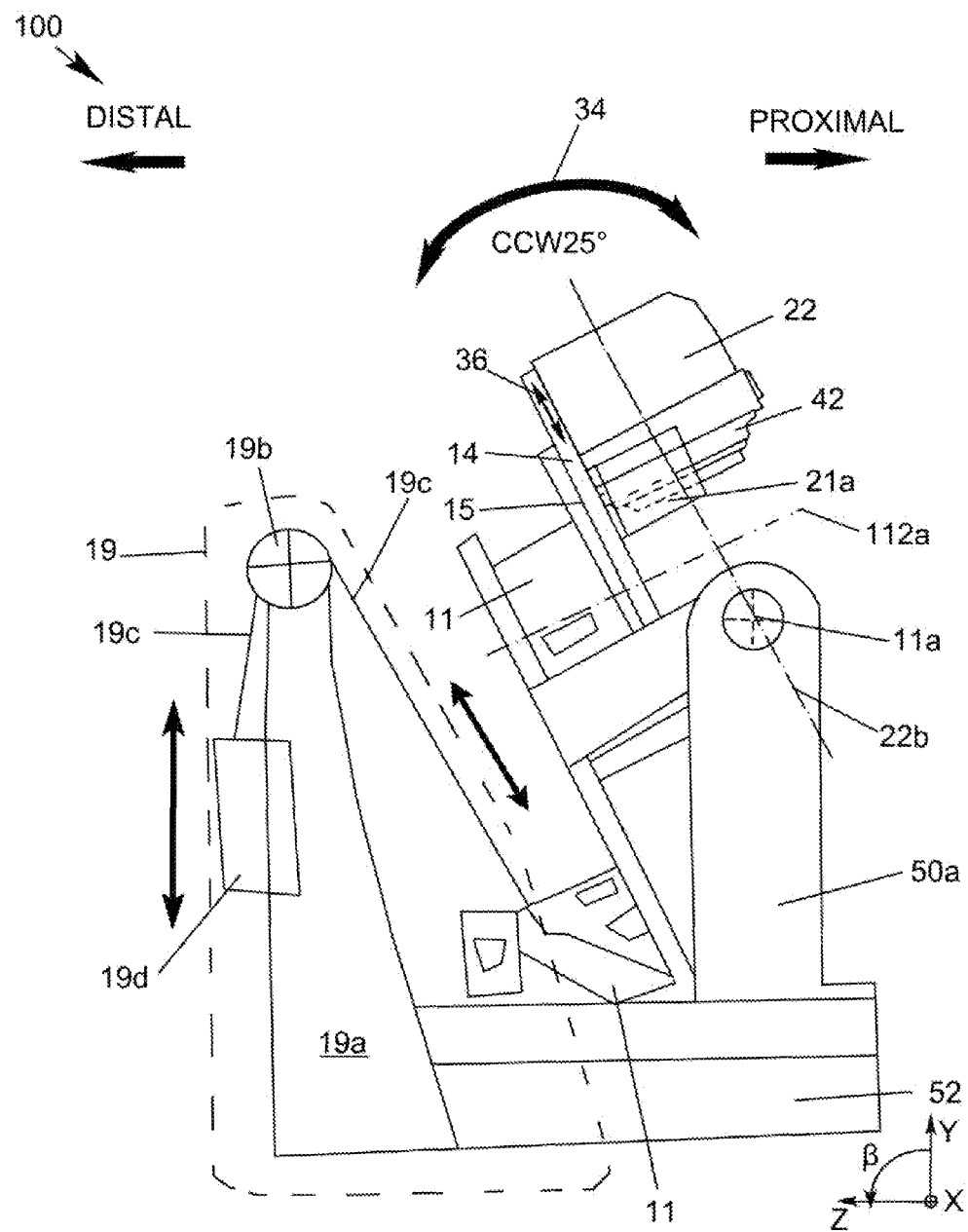
FIG. 3A illustrates a side view of another embodiment of the present invention SRRTA.

FIG. 3A illustrates a side view of yet another embodiment of the present invention SRRTA 100. In this example, the X-axis gantry pivoting driving mechanism is an X-axis gantry pivoting belt driving mechanism 19 coupled to and driving the DSG 11. The X-axis gantry pivoting belt driving mechanism 19 has a counter weight 19d coupled to the DSG 11 through a tension belt 19c riding upon a support pulley 19b that is supported on a distal support strut 19a. With this X-axis gantry pivoting belt driving mechanism 19 its required driving force can be substantially reduced due to the balancing action of the counter weight 19d against that of the DSG 11.

Figure 4:
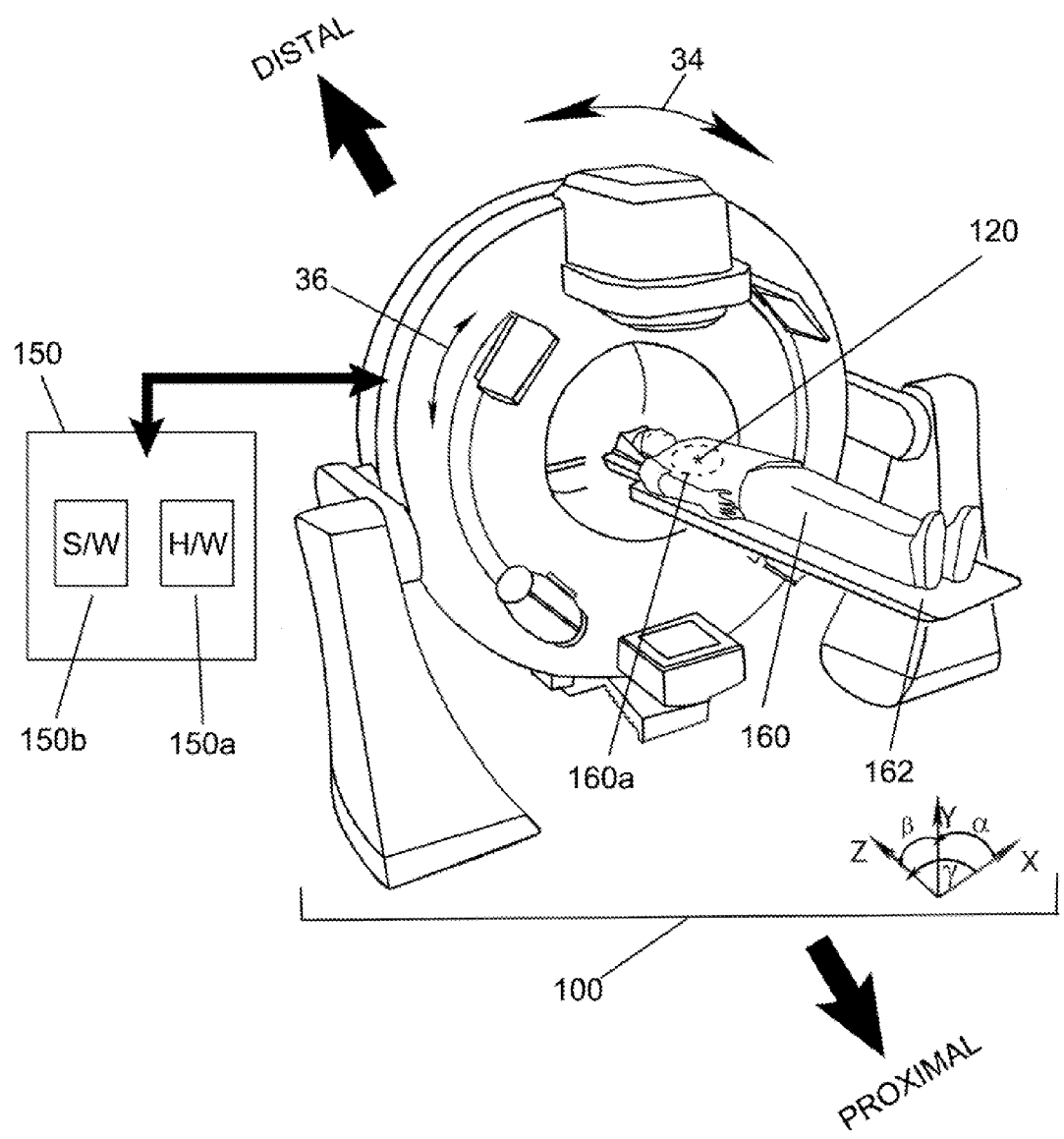
FIG. 4 illustrates the SRRTA, upon interfacing with an external electronic radiation therapy controller (ERTC), performs the function of image guided radiation therapy (IGRT).

FIG. 4 illustrates the present invention SRRTA 100, upon interfacing with an external electronic radiation therapy controller (ERTC) 150, performs the function of image guided radiation therapy (IGRT). The ERTC 150 has its ERTC hardware 150a and ERTC operating software 150b. For those skilled in the art, numerous details of the ERTC hardware 150a and ERTC operating software 150b known in the art are not shown here to avoid unnecessary obscuring details. Thus, upon placement, with a robotic couch 162 for example, of a patient 160 with his target organ 160a coinciding with the SRC 120 of the SRRTA 100 and upon activating the SRRTA 100 with ERTC 150, the SRRTA 100 can perform image guided radiation therapy (IGRT) with:

(A) A global α-radiation angle adjustment mode. Under this mode the α-coordinates of the rotatable therapeutic level radiation axis 22b and all rotatable imaging level radiation axes (20b and 21b) can be dynamically changed in unison through rotation of the proximal gantry face 114; and/or (B) An individualized α-imaging angle adjustment mode. Under this mode the α-coordinate of each individual rotatable imaging level radiation axis (20b or 21b) can be dynamically changed, through the rotation of its corresponding imaging level radiation-imaging pair [(20, 20a) or (21, 21a)] against the arc-shaped sub-rails 12a, 12b, independent of other rotatable imaging level radiation axes and the rotatable therapeutic level radiation axis 22b; and/or (C) A global β-radiation angle adjustment mode. Under this mode the β-coordinates of the rotatable therapeutic level radiation axis 22b and all rotatable imaging level radiation axes (20b and 21b) are dynamically changed in unison through rotation around the DSG-rotational axis 11a.

One example of the IGRT procedure is as follows. Upon placement of the patient's target organ 160a so that it coincides with the SRC 120 of the SRRTA 100, 3-dimensional organ images can be frequently acquired and updated so as to track any movement of the target organ 160a during the IGRT procedure. This is done by the ERTC 150 activating, through the ERTC hardware 150a, the imaging level radiation-generating and image-detection pair (20, 20a) and/or the imaging level radiation-generating and image-detection pair (21, 21a) each with its own desired illumination angle in α-coordinate and β-coordinate. The ERTC software 150b of the ERTC 150 can then computationally reconstruct target images of the target organ 160a in real time. With the real-time target images of the target organ 160a in hand, the ERTC 150 can now activate, through the ERTC hardware 150a, the therapeutic level radiation-generating and image-detection pair (22, 22a) with its desired therapeutic illumination angle in α-coordinate and β-coordinate and with its desired radiation dosage according to a pre-stored recipe in the ERTC software 150b.

In another embodiment under the present invention although not shown in the figures, two camera heads can be deployed upon the multi-leaf radiation collimator to view in the direction of the target organ 160a from a "bird's eye view (BEV) angle". The two camera heads can, in real-time, view and record numerous target organ 160a activities like breathing movements (rate, trajectory, location), creeping movements, common patient positional deviation, target organ contractions, etc. Furthermore, such viewed target organ activities can be, through proper processing by the ERTC software 150b, fed back to enhance 4-dimensional tracking ability of the present invention SRRTA 100.

An example of the fundamental operating parameters of the SRRTA 100, in conjunction with the ERTC 150, is as follows:

(1) Resolution of detected radiation images from the therapeutic level radiation-image detector 22a: More than 1024*1024*8bit.
(2) Rendition of displayed radiation image: Real-time, automatic display and storage.
(3) Positioning accuracy: Translation<0.5 mm, Rotation<0.5 degree.
(4) Image acquisition throughput: 1 frame/second.
(5) CPU calculation time of the amount of patient couch shift: about 15 seconds.
(Remark: Before commencement of radiation treatment, the patient plus tumor need to be aligned along with the radiation beam line. Thus, the ERTC 150 acquires and uses the patient images to calculate and check out the positional difference between the patient plus tumor and the radiation beam line then calculates a required positional shift there between for alignment. The ERTC 150 can then instruct a patient couch to "shift" or move into its aligned position.
(6) Accuracy of radiation dosage: >95%.
(7) Modes of radiation image detection: Single exposure, double exposure, and treatment procedure-directed exposure.

As a simplification of the present invention embodiment, only one pair of imaging level radiation-generation and radiation-detection can be installed, for example the Kilo-Volt level radiation-generating accelerator 20 and Kilo-Volt level radiation-image detector 20a. Another simplification is to have the Kilo-Volt level radiation-image detector 20a also performing the function of thus eliminating the Mega-Volt level radiation-image detector 22a. This can be accomplished by having an electrical control circuit of the SRRTA 100 positioning the Kilo-Volt level radiation-image detector 20a such that it respectively opposes the Kilo-Volt level radiation-generating accelerator 20 or the Mega-Volt level radiation-generating accelerator 22 on demand. To those skilled in the art, it should become clear by now that additional variations of the number of radiation-generating accelerators and radiation-image detectors can be flexibly configured as well according to demand.

As another embodiment, the Mega-Volt level radiation-image detector 22a can alternatively be mounted upon the ring-shaped guide rail 12 atop the Z-axis rotational support frame 14. Thus, the MV radiation level digital image detection planar board 22 can additionally reciprocally slide along the arc-shaped sub-rail (12a or 12b) while still following the Z-rotation 36 of the PSG 14. The advantage with this simplified mounting arrangement can be the reduction of spatial interferences among the various components of the SRRTA 100 or its increased operability.

As a general remark, all the aforementioned embodiments are only preferred embodiments under the present invention. To those skilled in the art, therefore, it is pointed out that numerous additional variations and improvements, other than those already described above, are possible and as such, without departing from the spirits of the present invention, should all be deemed covered thus protected by the present invention.

What is claimed are:

1. A gantry based radiation therapy apparatus with a single spherical rotation center-rooted spherical rotational radiation therapy apparatus (SRRTA), where the gantry having a hollow cylindrical gantry bore, expressing the SRRTA in a combined X-Y-Z Cartesian coordinates and an accompanying polar coordinates (r-α-β-γ) where the Z-axis is parallel to a longitudinal axis of the hollow cylindrical gantry bore and pointing from the proximal end of the gantry toward its distal end, the Y-axis is pointing vertically upwards and the X-axis is pointing horizontally and parallel to a proximal end face of the gantry and wherein a is an angular coordinate in the X-Y plane, β is an angular coordinate in the Y-Z plane and γ is an angular coordinate in the Z-X plane, the SRRTA comprises:
a) a multi-axial gantry of a substantially cylindrical shape with an annular X-Y cross section and a hollow cylindrical bore with a longitudinal bore axis, the proximal face of said multi-axial gantry being rotatable around the longitudinal bore axis thus along α-coordinate;
b) the proximal gantry face having:
b1) one or more rotatable, around the longitudinal bore axis thus along α-coordinate, annularly opposing pairs of therapeutic level radiation-generating accelerator and its corresponding therapeutic level radiation-image detector, with each pair defining a therapeutic level radiation-imaging pair and a rotatable therapeutic level radiation axis between the two;

b2) at least two annularly opposing arc-shaped sub-rails mounted thereon and centered around the longitudinal bore axis; and b3) at least two rotationally slidable, against the arc-shaped sub-rails thus along α-coordinate, annularly opposing pairs of imaging level radiation-generating accelerators and their corresponding imaging level radiation-image detectors, with each pair defining an imaging level radiation-imaging pair and a rotatable imaging level radiation axis between the two; and c) the Z-coordinates of all the therapeutic level radiation-imaging pairs and all the imaging level radiation-imaging pairs are selected such that all the therapeutic level radiation axes and all the imaging level radiation axes intersect at a single spherical rotation center (SRC) located at a predetermined point along the longitudinal bore axis whereby, upon placement of a patient with his target organ coinciding with the SRC and upon interfacing the SRRTA with an external electronic radiation therapy controller (ERTC), the SRRTA functions to perform image guided radiation therapy (IGRT) with:

(A) a global α-radiation angle adjustment mode wherein the α-coordinates of all therapeutic level radiation axes and all imaging level radiation axes are dynamically changed in unison through rotation of the proximal gantry face; and/or (B) an individualized a-imaging angle adjustment mode wherein the α-coordinate of each individual imaging level radiation axis is dynamically changed, through the rotation of its corresponding imaging level radiation-imaging pair against the arc-shaped sub-rails, independent of other imaging level radiation axes and all the therapeutic level radiation axes.

2. The SRRTA of claim 1 further comprises an X-axis gantry pivoting base support mechanism coupled to and supporting the multi-axial gantry and an X-axis gantry pivoting driving means coupled to and driving the distal end of the multi-axial gantry, said multi-axial gantry comprises a proximal sub-gantry (PSG) and a distal sub-gantry (DSG) with:

the PSG rotatably, around the longitudinal bore axis, supported by the DSG through a bearing interface there between;

the DSG pivotably, around a DSG-rotational axis parallel to the X-axis thus along the β-coordinate, supported by the X-axis gantry pivoting base support mechanism and driven through the β-coordinate by the X-axis gantry pivoting driving means whereby the SRRTA additionally functions to perform IGRT with:

(C) a global β-radiation angle adjustment mode wherein the β-coordinates of all therapeutic level radiation axes and all imaging level radiation axes are dynamically changed in unison through rotation around the DSG-rotational axis.

3. The SRRTA of claim 2 wherein, to insure structural rigidity of the multi-axial gantry and locational accuracy of the SRC, the X-axis gantry pivoting base support mechanism comprises at least two base support mechanisms each having a pivot-bearing engaging the DSG and a support strut supporting the pivot-bearing.

4. The SRRTA of claim 3 wherein, to further strengthen structural rigidity of the multi-axial gantry and increase locational accuracy of the SRC, the X-axis gantry pivoting base support mechanism further comprises a bottom base for affixing the support struts thereupon.

5. The SRRTA of claim 1 wherein the proximal gantry face has one annularly opposing pair of therapeutic level radiation-generating accelerator and its corresponding therapeutic level radiation-image detector.

6. The SRRTA of claim 5 wherein the proximal gantry face has two annularly opposing arc-shaped sub-rails.

7. The SRRTA of claim 6 wherein each arc-shaped sub-rail subtends an α-range from about 20 degrees to about 150 degrees.

* * * * *